United States Patent
Schwartz

[19]

[11] Patent Number: 5,881,461
[45] Date of Patent: Mar. 16, 1999

[54] NAIL CUTTER/CLIPPER FOR TREATING INGROWN NAILS AND HANG NAILS AND/OR PREVENTING INGROWN NAILS

[76] Inventor: Stanford Schwartz, 23708 3rd Pl., West Bothell, Wash. 98021

[21] Appl. No.: 876,620

[22] Filed: Jun. 14, 1997

[51] Int. Cl.⁶ .................................................. A45D 29/02
[52] U.S. Cl. .................................................................. 30/28
[58] Field of Search ................................ 30/26, 28, 124, 30/254, 255

[56] References Cited

U.S. PATENT DOCUMENTS

| | | | |
|---|---|---|---|
| 327,065 | 9/1885 | Burton | 30/28 |
| 702,516 | 6/1902 | Wilcox | 30/28 |
| 762,725 | 6/1904 | Kaufmann | 30/28 |
| 2,507,345 | 5/1950 | Meesook | 30/28 |
| 2,521,027 | 9/1950 | Sorensen | 30/28 |
| 3,093,898 | 6/1963 | Smith | 30/28 |
| 4,674,486 | 6/1987 | Hoffman | 602/31 |
| 4,936,322 | 6/1990 | DeSantis | 30/27 |
| 4,964,213 | 10/1990 | Suggs | 30/28 |
| 4,980,975 | 1/1991 | Hodson | 30/254 |
| 5,012,799 | 5/1991 | Remmen | 602/30 |
| 5,226,433 | 7/1993 | Garcia-Carree | 132/73 |
| 5,437,679 | 8/1995 | Gaillard | 30/28 |

FOREIGN PATENT DOCUMENTS 8356 of 1898 United Kingdom .

*Primary Examiner*—Hwei-Siu Payer

[57] ABSTRACT

A nail cutter/clipper for use in treating ingrown nails, hang nails, and/or preventing ingrown nails. In a first embodiment, the nail/cutter includes first and second handles mated at a gudgeon in an X-shaped configuration. The first and second handles are joined to opposed nail cutter heads, and each nail cutter head has a V-shaped blade that defines a void or receptacle for receiving nail cuttings. The nail cutter heads cut a V-shaped notch in a nail when actuated by a user grasping the handles. A second embodiment includes an upper member joined to a lower member at a rearward end with a fastener. At their forward ends, these members each include a V-shaped cutter blade that defines a void, and when the cutter blades are forced together on a nail, a corresponding shaped notch is cut in the notch and the trimming is captured in the cutter blades. A third embodiment is similar to the first embodiment, except that the first and second handles are U-shaped, and the nail cutter heads are pivotally mounted to the handles, so that when not in use, the handles can be rotated about the pivot mountings, so that the nail cutting heads are stored protectively within the handles.

24 Claims, 11 Drawing Sheets

NAIL CUTTER/CLIPPER FOR TREATING INGROWN NAILS AND HANG NAILS AND/OR PREVENTING INGROWN NAILS

BACKGROUND-FIELD OF INVENTION

This invention relates to a nail cutter/clipper devices. More specifically, a nail cutter/clipper device and associated method for treating ingrown nail and/or preventing ingrown nails.

PRIOR ART REFERENCES

Presently, there is a plurality of devices and methods for treatment of ingrown nails. The ingrown nail is a condition in which the edge of the nail grows into the soft tissue of the digit, causing inflammation, sensitivity, soreness and, on occasions, an abscess. In the treatment of ingrown nails a popular method used chemical adhesives and members to restructure supports; another used cutters, clippers, scissors, and unique forms to remove sections of the nail. Some of the encountered problems are as follows: use of chemicals, Albeit toxic and offensive odors, required safety precautions, time consuming processes, costly materials, invasive procedures into a painful area, and requires additional healing time.

One such method, which is described in U.S. Pat. No. 4,674,486 to Ronald G. Hoffman, method for correcting ingrown toe nails by covering a portion of the nail surface with adhesive; albeit, the ingrown nail may be on both sides, of the nail which creates a problem, with the sheets and the adhesive; albeit, the use of Chemicals would require safety precautions. Then a layer of material is applied to the adhesive, to adhere to the side edges of the nail; the material urges the side edges of the nail upward, to flatten the nail, and eliminate the involution of the edges of the nail. Albeit, this method is time consuming. Albeit, the just described process is invasive, to the sensitive surrounding area of the ingrown nail.

One such device, which is described in U.S. Pat. No. 4,936,322 to Damian G. De Santis, comprises a hollow rod having a depressor and separator surface and safety knife surface. The safety knife cuts portions of the ingrown nail. The separator surface, depresses and separates the soft tissue to expose the ingrown nail portion, and the device may include a serrated surface, to smooth any burrs from the cut nail surface. Albeit, the devices serrated surface could be a breeding ground for germs and bacteria. Albeit, the process is invasive to an ingrown nail, and the sensitivity of surrounding area. Albeit, this device would be difficult to use by some consumers, because of the specific angle required to cut the nail.

Another such device and method, which is described in U.S. Pat. No. 4,964,213 to Patricia A Suggs, comprise a nail cutting device and associated method for treating and/or preventing ingrown nails. The nail cutting device member having an upper jaw with a protruding blade. Albeit, cutting of additional nail surface more than required. A second member having a lower jaw anvil, inserts the nail between the blade and the anvil, actuating the blade through the nail to produce a notch. Albeit, the cutting blade protrudes beyond the notch thus cutting additional nail anterior, making ragged nail edges. Albeit, the blade and anvil may produce a blockage of nail clippings between the anvil and blade.

Another such device and method, that is described in U.S. Pat. No. 5,012,799 to Werner Remmen, is a appliance having a V-shaped bridge engaging the nail to exert leverage, causing the nail corners to become uplifted. Albeit, the just described process is invasive to the sensitive surrounding area of the ingrown nail, The device covers the entire nail, which may not be necessary. Albeit, this is used only on toe nails.

Another such device and method, which is described in U.S. Pat. No. 5,226,433 to Jaun J Garcia-Carree, consists of a device and process for treatment of ingrown nails, in which a portion of the nail is separated from the affected underlying epidermis area of the affected finger or toe, then the device is inserted over the released edge of the nail. Albeit, the just described process is invasive to the sensitive, surrounding area of the ingrown nail. The method needs extended time beyond initial healing to ensure rehabilitation of the adjacent tissues before the nail is allowed to contact, thereby avoiding a relapse. Albeit, extended time beyond the initial healing is required, and the process is time consuming.

OBJECTS AND ADVANTAGES

Accordingly, several objects and advantages of my invention are as follows: to provide a simpler, more reliable cutter/clipper device, to be right and/or left handed, easy to use, reduction of invasiveness, no chemicals, save time, cleanliness, a preferred method of treating and/or preventing ingrown nails, method of treating hang nails, solution to an unrecognized problem.

Still further objects and advantages will become apparent from a consideration of the ensuing description and accompanying drawings.

REFERENCE NUMERALS

Nail cutter/clipper
10 nail cutter/clipper
12 handle
14 handle covering
16 hole
18 cutter blade
20 cutter head
22 spring hole
24 spring
25 eye hole
26 eye
27 hook
28 handle
30 handle covering
32 hole
34 cutter head
36 void
38 gudgeon
39 eye hole
40 eye
42 cutter blade
44 void
46 spring hole
48 toe nail
50 V cutout
52 toe hang nail
54 toe nail
56 V cutout
58 thumb
60 nail
62 V cutout
64 hang nail
66 toe hang nail
68 finger hang nail
Nail clipper/cutter
70 nail clipper/cutter 72 member
73 member bend
74 forward end portion
76 jaw
78 cutter blade
80 void
82 member
83 member bend
84 forward end portion
86 jaw
88 cutter blade
90 void
92 nail
93 hang nail
94 actuator free end portion
96 cutout
98 lever arm actuator
100 pivot bolt
102 member hole
104 lever end portion
106 lever bend
107 rivet
108 protruding member
110 direction force arrow
112 member hole
Folding Nail clipper/cutter
114 folding nail clipper /cutter
116 U-shaped handle
118 cutter head portion
120 gudgeon for handle
122 handle hole
124 cutter head protrusion hole
126 head portion hole
128 head portion gudgeon
130 lower void
132 cutter blade
134 protrusion hole
136 protrusion arc
138 notch in handle
140 spacer
142 U-shaped handle
144 cutter head portion
146 handle gudgeon
148 handle hole
150 cutter head protrusion hole
152 gudgeon hole
154 void
156 cutter blade
158 protrusion arc
160 notch in handle
162 spacer
164 cutter head protrusion
166 cutter head protrusion
168 protrusion
170 protrusion
172 tongue
174 tongue

Preferred First Embodiment—Description

Figure 1:
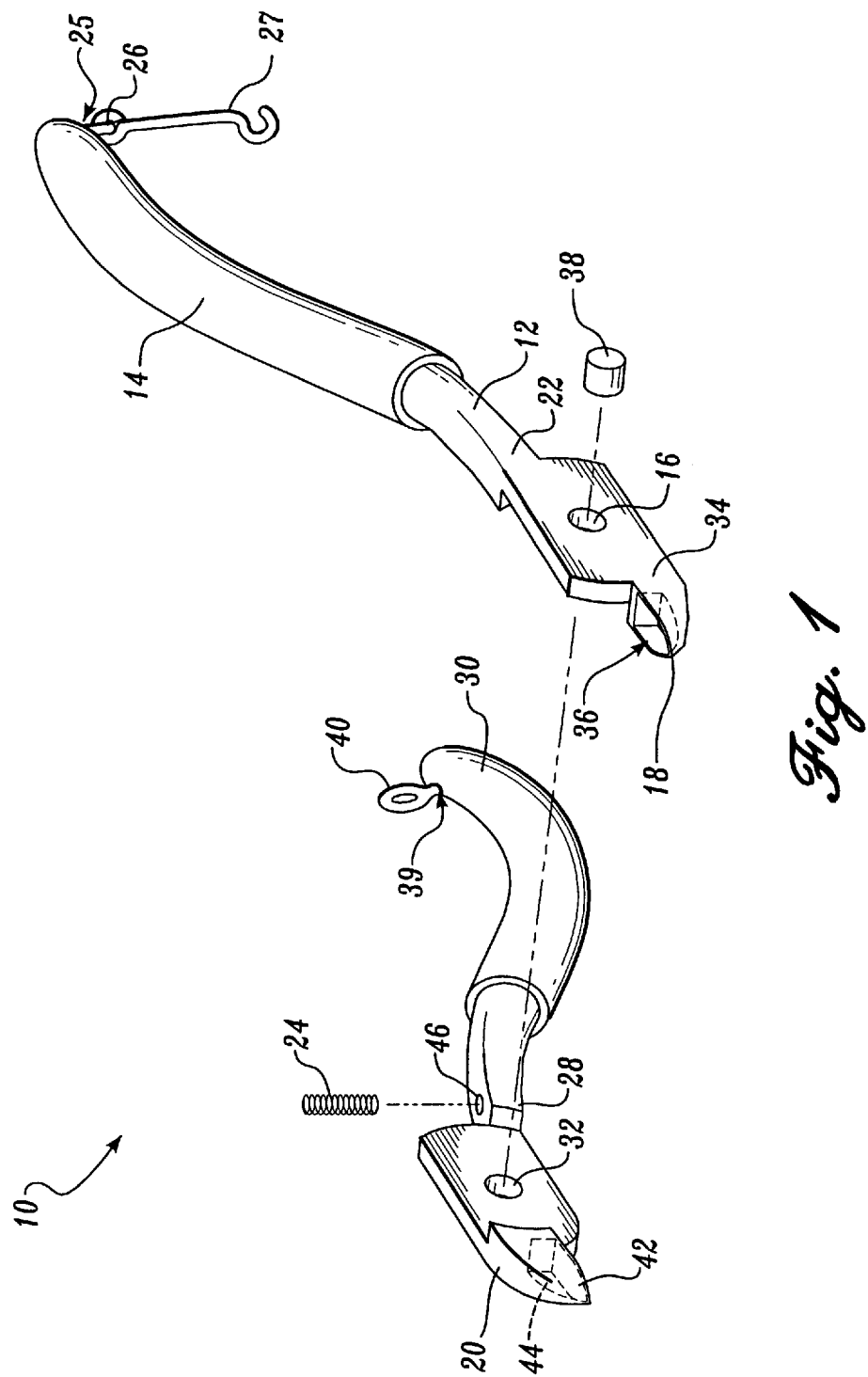
FIG. 1 is an exploded isometric view of the nail cutting device of the present invention.

The general description of FIG. 1, shows an exploded view of cutter/clipper device 10, a support member 12 with V-shaped cutter blade 18, a support member 28 with a V-shaped cutter blade 42, a gudgeon 38, for joining said equal length support member 12, and said support member 28 in an x shaped placement.

A nail cutter/clipper of the present invention is illustrated in FIG. 1 is a preferred specific embodiment, showing the first portion of a cutter/clipper device 10 with an arched support member, arced handle member 12, a cutter head, cutter head portion, or nail cutter head 34, a V-shaped void, V-void or void 36, a V-shaped blade, V-blade or blade 18, a hole, cutter hole or gudgeon hole 16, a hole, or spring hole 22, eye hole or hole 25. All of the above fabricated parts to be made from die-casted surgical steel. The second portion of a cutter/clipper device 10 with a handle, structural member or arched handle member 28, a cutter head, cutter head portion, or nail cutter head 20, a V-shaped void, V-void or void 44, a cutter blade, a V-shaped blade, V-blade or blade 42, a hole, cutter head hole or gudgeon hole 32, a hole, or spring hole 46, eye hole, or hole 39. All of the second portion fabricated from die-casted surgical steel. The said first and second portions are mated at the fulcrum point by means of said gudgeon 38 made from die-casted surgical steel fitted into said hole 16 and said hole 32. The said handles 12 and 28 consist of arc shaped portions. A spring 24, is inserted into said hole 22, and inserted into said hole 46, which lock into said hole 22 and said hole 46 which holds said nail cutter/clipper device 10 into an open position. A locking portion consisting of: an eye 26 and hook 27, are inserted into hole 25, an eye 40, inserted into hole 39, and hook 27 mates with said eye 40, which holds said cutter device 10 in a closed blade position.

The approximate overall dimensions of the nail cutter device in one commercial embodiment were as follows: from handle to the cutter tip overall length 100 mm, the widest point of the handles from outer edge to the outer edge is 44 mm, 42 mm radius at high point of handle arc, cutter blade 9 mm long, cutter head 25 mm long and thickness 5 mm, gudgeon 5 mm diameter outside dimension, the mating plate's 2.5 mm each, material not known, manufactured in Germany.

Figure 2:
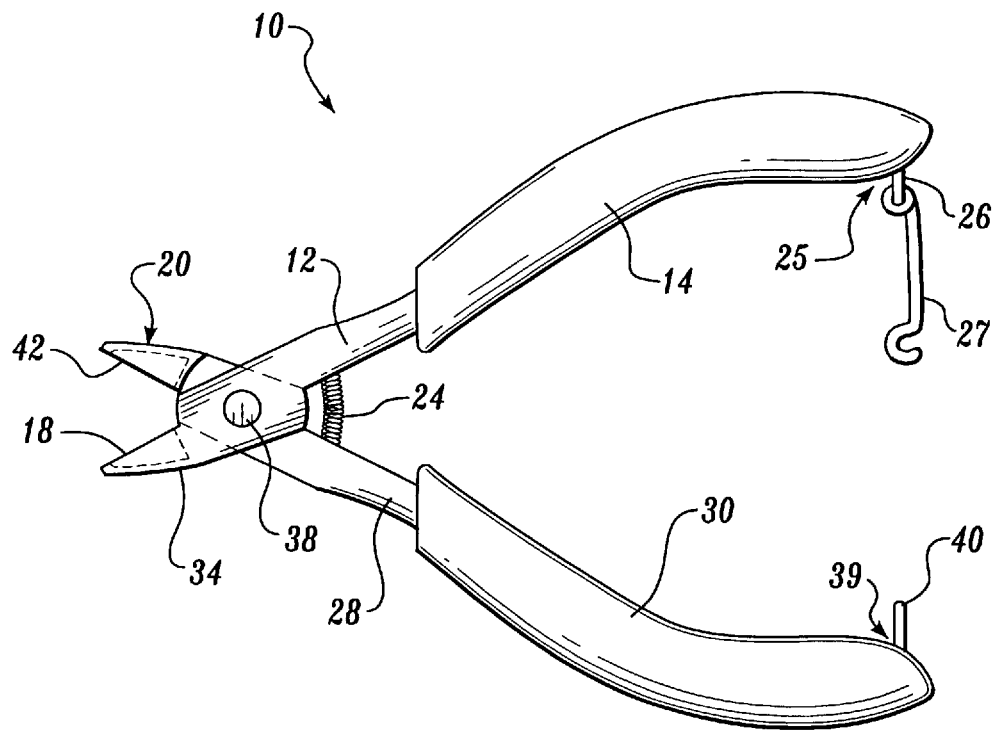
FIG. 2 is a plan view of the nail cutting device of the present invention.

FIG. 2 shows the assembled mating portions in a plan view, said handle 12, and said handle 28, and crossing in the shape of an X joined by means of said gudgeon 38, said cutter device 10, held in an open position by said spring 24, A handle covering 14, a handle covering 30, is made for hand comfort and fabricated from latex or selected elastomer material. The said eye 26, said hook 27, said eye 40, and are selectively sized and inserted into said hole 39, means to lock the nail cutter 10 in a closed position.

Figure 3:
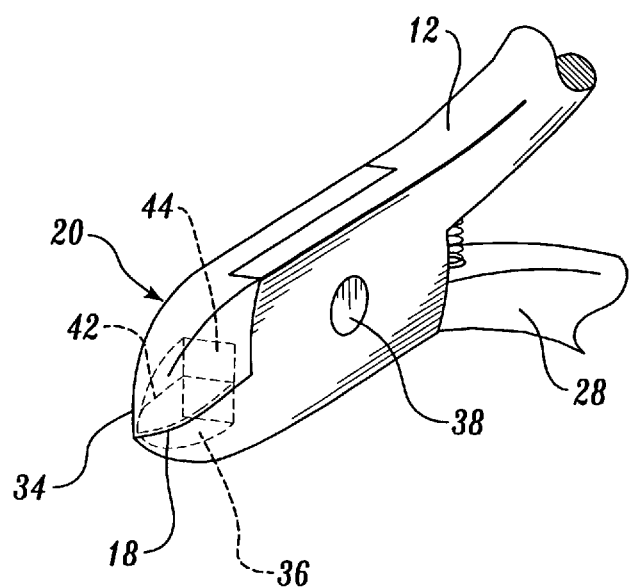
FIG. 3 is an enlarged detail of the nail cutting device of the present invention.

FIG. 3 shows partial enlarged detail of the said nail cutter head portion in a closed position. In accordance with the invention the said nail cutter head 34, and said nail cutter head 20, and provide space at the fulcrum point, for said holes 16 and 32, and said gudgeon 38, mates into said holes 16 and 32. The nail cutter head portion 34, and said nail cutter head portion 20, also consist of said V-shaped void 36, and said V-shaped void 44, and said cutter blade 18, said cutter blade 42. In the preferred die-casted form is surgically sharp blades, said cutter blade 18, said cutter blade 42, is beveled from the said V-shaped void 36 and said V-shaped void 44, to the outside surface of said cutter head 34, and cutter head 20.

Figure 4:
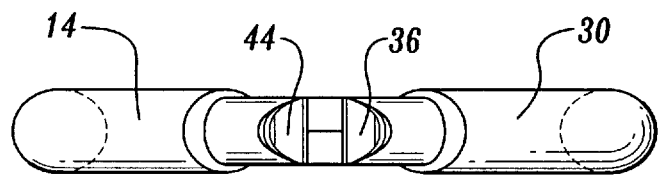
FIG. 4 is a view looking into the open nail cutting device blades of the of the present invention.

FIG. 4 shows the view looking into nail cutter device in an open position, the preferred sixty degree angle for said V-shaped void 36, said V-shaped void 44 illustrates the V contour of said cutter blade 18 and said cutter blade 42.

Figure 5:
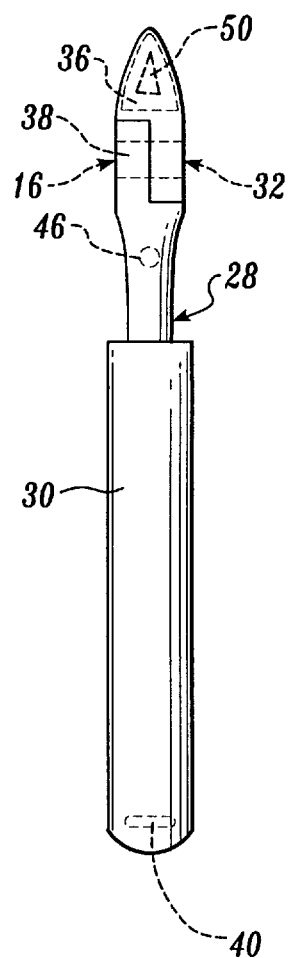
FIG. 5 is a side elevation view of the nail cutting device of the present invention.
Figure 6:
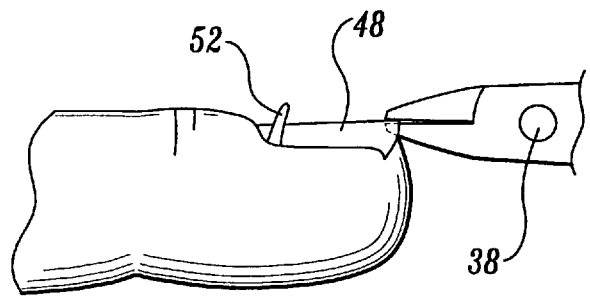
FIG. 6 is a partial side view of the human toe nail, illustrating the nail cutting in accordance with the method of the present invention.
Figure 6A:
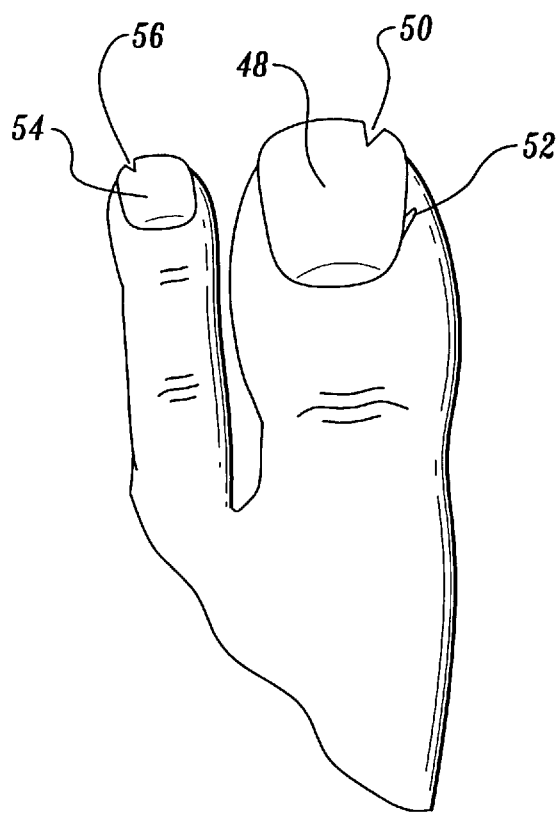
FIG. 6A is a partial plan view of the human foot nails, illustrating the nail cut in accordance with the method of the present invention.
Figure 6B:
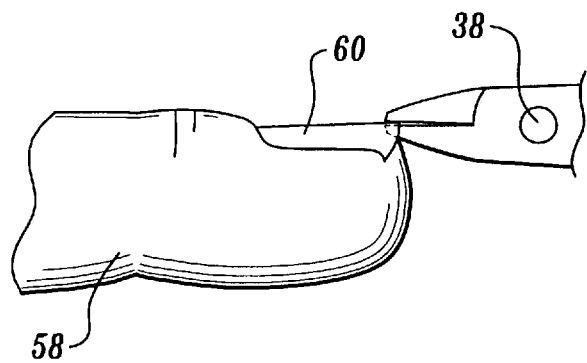
FIG. 6B is a partial side view of the human finger nail, illustrating the nail cutting in accordance with the method of the present invention.
Figure 6C:
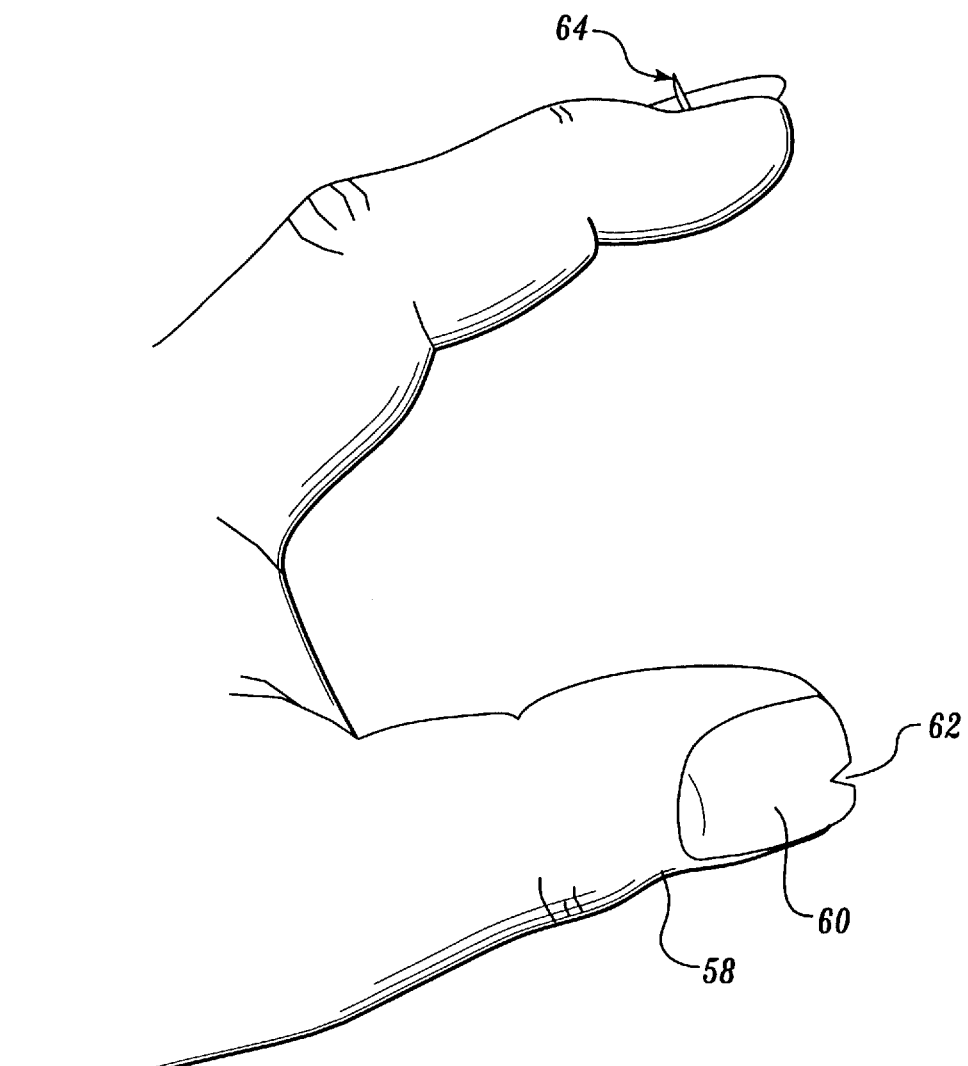
FIG. 6C is a partial view of the human hand, illustrating the finger nail cut in accordance with the method of the present invention, and the hang nail to be cut in accordance with the method of the present invention.
Figure 6D:
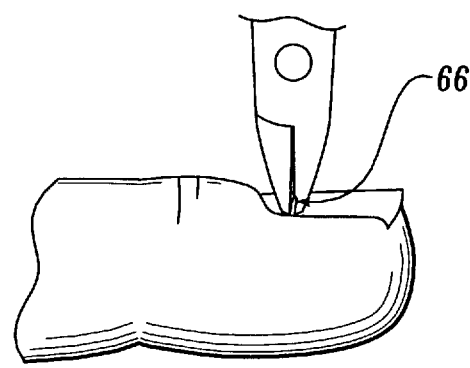
FIG. 6D is a partial side view of a thumb nail, illustrating an ingrown nail, and hang nail being cut in accordance with the method of the present invention.
Figure 6E:
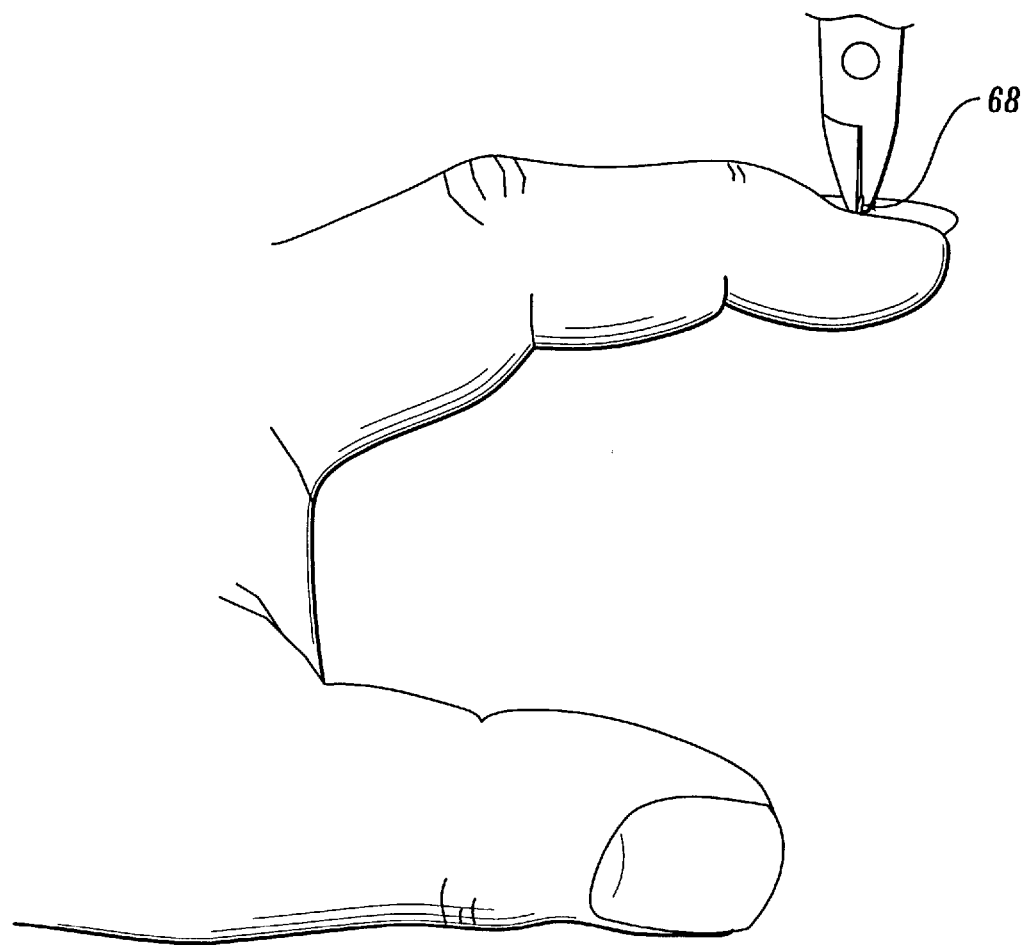
FIG. 6E is a partial view of the human hand, illustrating a hang nail being cut in accordance with the method of the present invention.

FIG. 5 shows the side elevation of the nail cutter device 10, and by increasing the space available for the larger preferred said void 36 and the larger said void 44 and this allows the smaller nail chip 50 to freely move in the larger said void 36 and 44, thereby capturing the smaller nail chip allowing for proper disposal at a later time, FIG. 6 is a partial side view of the human toe nail illustrating the nail cutting in accordance with the method for treating the ingrown nails.

FIG. 6-A shows a plan view of the human toe nail illustrating the nail cutting in accordance with the method for treating the ingrown nails FIG. 6-B shows a partial side view of the human finger nail illustrating the nail cutting in accordance with the method for treating the ingrown nails.

FIG. 6-C shows a partial view of the human thumb nail and figure nail illustrating the nail cutting in accordance with the method for treating the ingrown finger nails FIG. 6-D shows a partial side view of the human thumb nail illustrating the nail cutting in accordance with the method for treating the hang nails.

FIG. 6-E shows a partial view of the human hand illustrating the preferred method for treating the hang nails.

Preferred First Embodiment—Operation

Operation and use of the nail cutter/clipper device and associated method for treating ingrown nails and hang nails and/or preventing ingrown nails is simple and straightforward. Open the nail cutter device by removing hook 27 from the eye 40 and the cutter device will be held in an open position by means of a spring 24 as shown in FIG. 2 place the open cutter blades with nail to be treated proximate to the side of the ingrown nail and perpendicular to the nails arc, and place open blades between the nail, the tip of the cutter blade is inserted to a proximate comfortable depth in the nail and when force is applied by hand or machine to the handles in a closing motion the device will close together rotating about the gudgeon 38, and by increasing the force on the handles and this increases the forces on the cutter head portion, increase the force cutting through the nail, thereby capturing the nail cutting, and the nail cutter blades will appear as shown in FIG. 6, then decrease the force to open the blades as shown in FIG. 2, dispose the nail cutting 50, the finished cut will appear as shown in FIG. 6-A.

The preferred method for treating the hang nail is to open the nail cutter as shown in FIG. 6-D, FIG. 6-E and place the cutter blades proximately ninety degrees perpendicular to the hang nail to be treated shown in position 66 and 68, the side of the nail cutter tip held against the base of the hang nail, then close the nail cutter by applying pressure on handles, the nail cutter blades will appear as shown in FIG. 6-D, increase the force to cut the hang nail off, decrease the force to open the blades as shown in FIG. 2, dispose the hang nail cutting.

First Embodiment Conclusions, Ramifications, and Scope

Accordingly, it can be seen that the nail cutter/clipper device, is easy to use, without the use of chemicals, and reduces the invasive nature of treating and/or preventing ingrown nails. Furthermore, the nail cutter/clipper device has additional advantages in that:

it provides simpler, more reliable, easy use;

it provides use for people with certain disabilities;

it provides two V-shaped cutter blades for true cutter action on different nail textures;

it provides two sharp V-shaped cotter blades for medical precision;

it may also be used for cutting off hang nails and/or other felons;

it provides stainless steel cutter blades for easy medical sterilization;

it provides long lasting stainless steel;

it allows left or right handed use;

it saves time over other methods;

it provides self containment of nail cuttings for later disposal;

it permits use on primates and other animals;

it provides method of treating and/or preventing ingrown nails;

it provides a handle covering for comfort;

it provides rust resistant stainless steel;

it provides fast results;

it permits use on two (right & left sides) simultaneously ingrown nails on a single nail;

it provides a slip resistant handle covering;

Although the description above contains many specificity's, these should not be construed as limiting the scope of the invention but as merely providing illustrations of some of the presently preferred embodiments of this invention. Various other embodiments and ramifications are possible within it's scope. For example, a resilient metal, or glass reinforced nylon could be used in place of surgical steel. Also the handle covering could be made from a rubber material, selected elastomer material, or no covering in place of latex, a sheet metal cutter or other tool, a,)-mouth cutter/clipper blade, shaped trapezoid. Also the symmetrical sixty degree V-shaped cutter blade angle could be seventy five degrees, Nail clipper size can vary small medium or large, a means to actuate the actuator for people with disabilities, a mechanical means to increase ratio of force, for use on primates, and other animals with human like nails The scope of foregoing description of the preferred embodiment of the invention has been presented for the purposes of illustration and description, it will be understood that there is no intention to limit the invention to such disclosure but rather it is intended to cover all alternate construction and modifications falling within the scope and the spirit of the invention as defined in the appended claims.

First Embodiment Summary

A nail cutter/clipper device comprising of a handle, cutter head, V-shaped blade and hole as a first portion, and the second portion handle, cutter head, V-shaped blade and hole in an X shaped placement mated by means of a gudgeon and the associated method for treating ingrown nails and hang nails and/or preventing ingrown nails.

Preferred Nail Clipper Second Embodiment—
Description

A nail clipper/cutter device incorporating various of the present invention is illustrated generally at 70 in the figures. The said clipper/cutter device 70 makes a cutout 96 in the nail of a toe or finger. As a method for treating ingrown nails and hang nails and/or preventing ingrown nails, as will be discussed in detail below. The said nail clipper/cutter device 70 comprises an upper member 72, having an upper forward end portion 74, an upper jaw 76, an upper cutter blade 78 which, in the preferred embodiment defines the upper void 80. A lower member 82, having a lower forward end portion 84, a lower jaw 86, a lower cutter blade 88, which in the preferred embodiment defines the lower void 90. The said upper member 72 and said lower member 82 are joined at, or proximate, their rearward end portions, with a fastener such as a rivet 107.

The approximate overall dimensions of the nail clipper in one commercial embodiment were as follows: from handle to the cutter tip, the overall length 80 mm by 12 mm wide, the actuator is 3 mm, cutter blade 14 mm long, cutter blade 2 mm high and thickness 2 mm, pivot bolt 4 mm diameter 17 mm high, material not known, manufactured by Revlon.

Figure 7:
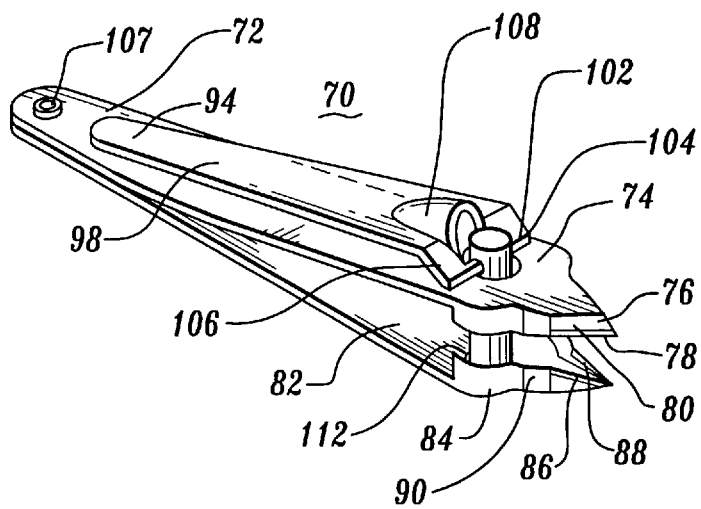
FIG. 7 is a perspective view of the nail clipper/cutter device of the present invention.
Figure 7A:
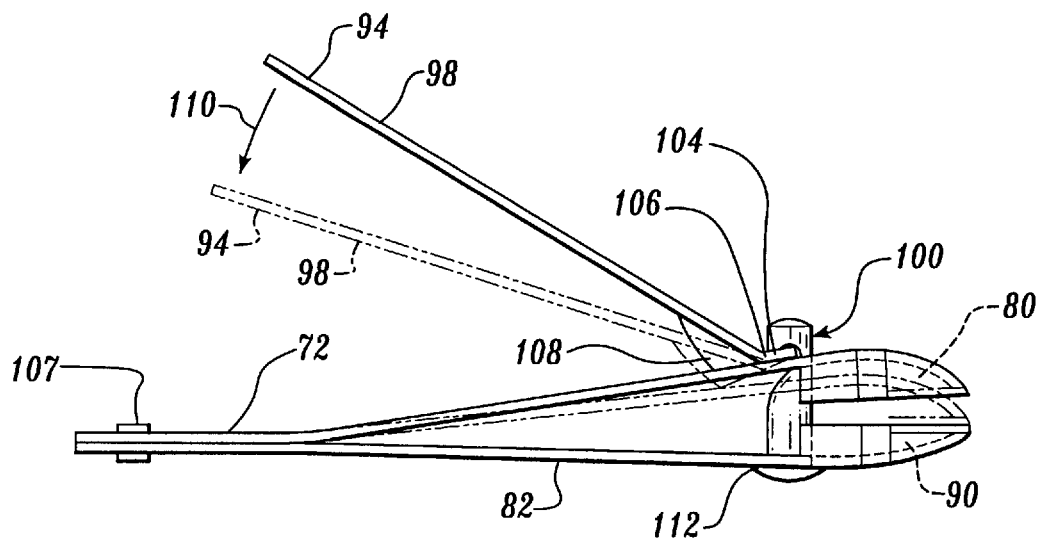
FIG. 7A is a side view of the nail clipper/cutter device of the present invention.
Figure 7B:
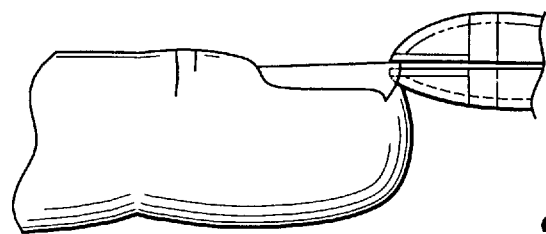
FIG. 7B is a partial side view of a thumb nail, illustrating an ingrown nail being cut in accordance with the method of the present invention.
Figure 7C:
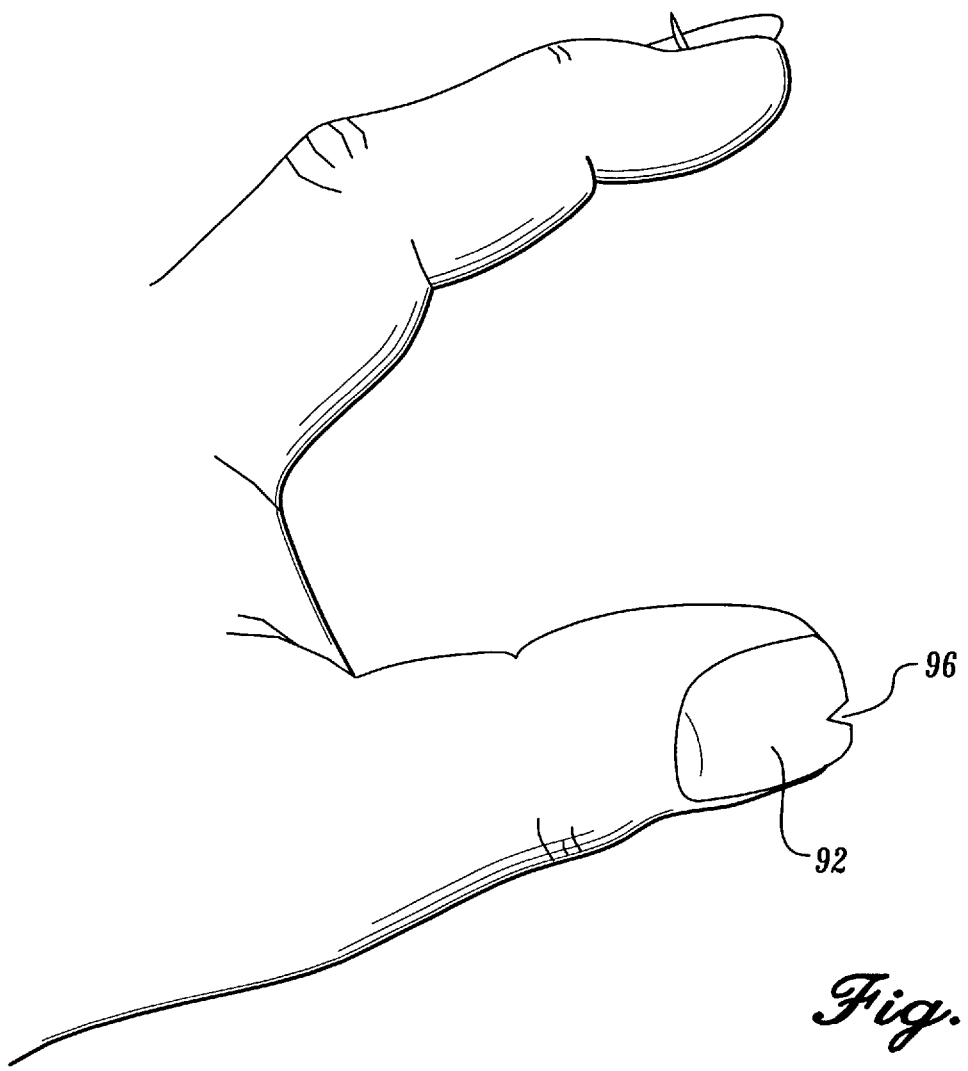
FIG. 7C is a partial view of the human hand, illustrating the finger nail to be cut in accordance with the method of the present invention, and a hang nail to be cut in accordance with the method of the present invention.

As best illustrated in FIG. 7-A, the members 72 and 82 are configured such that their forward end portions 74 and 84, respectively spaced apart a selected distance. They are preferably fabricated of surgical steel. Whereas the forward end portions 74, and 84 brought together.

As best illustrated in FIG. 7, the said upper forward end portion 74, defines the said upper jaw 76 provided with a protruding said V-shaped cutter blade 78, having a downwardly disposed cutting edge. Further, the said lower forward end portion 84, defines the said lower jaw 86 provided with a protruding said lower cutter blade 88, having an upwardly disposed cutting edge. In the preferred embodiment said cutter blade 78 and 88, so as to produce a V cutout 96 in the nail being cut. In order to bring the said forward end portions 74 and 84 together to perform the cutting operation. The said device 70 is provided with an actuator means for overcoming the outward bias of the members 72 and 82, and forcing the direction of said upper cutter blade 78 in the direction of said lower cutter blade 88. In the preferred embodiment such actuator means comprises a lever arm 98 secured to said members 72 and 82 with a pivot bolt 100.

More specifically the said bolt 100 is rotatable and slideably received through a hole 102 provided in said upper member 72 proximately the said forward end portions 74. The said lever arm 98 is pivotally secure proximate to said lever end portion 104, to the said bolt 100 above the said upper member 72. Further the said lever arm 98 is provided a bend 106 proximate the lever end portion 104 such that the said lever arm 98 diverges from the said upper member 72 and is also provided in the preferred embodiment with a protruding member 108 which selectively engages the said upper member 72 and serves as a fulcrum for the said lever arm 98.

Accordingly, it will be understood that when the free end portion 94 of the lever arm 98 is pivoted in the direction of the arrow 110 (See FIG. 7-A) protruding member 108 forces the said upper member 72 downwardly and forces the said cutter blade 78 against said cutter blade 88 of said lower member 82. Thus the cutting of the nail is accomplished by placing the nail between the cutter blade 78 against cutter blade 88 and pivoting the lever arm 98 to bring the cutter blade 78 against cutter blade 88 together. As discussed above, the pivot bolt 100 is rotatably received in the holes 102 and 112. This allows the lever arm 98 to be placed in a storage position as illustrated in FIG. 7. This is accomplished by rotating the lever arm 98 one hundred eighty degrees (180) from the position illustrated in FIG. 7-A, and pivoting the lever arm 98 back against the upper member 72.

Preferred Nail Clipper Second Embodiment—
Operation

Operation and use of the nail clipper/cutter device 70 and associated method for treating ingrown nails and hang nails and/or preventing ingrown nails is simple and straightforward. Open the nail clipper/cutter device by lifting lever arm 98 from the rearwardly position, flip lever arm 98 one hundred eighty degrees forwardly towards the cutter blades tips 78 and 88, then rotate the lever 98 one hundred eighty degrees backwards the said lever 98 will rest on the said protruding member 108 and will be resting on said upper member 72. The cutter device 70 will be held in an open blade position by means of a said protruding member 108 as shown in FIG. 7-A. Place the open cutter blades with nail to be treated proximate to the side of the ingrown nail and place open blades in between the nail, the tip of the cutter blades is inserted to a proximate comfortable depth in the nail and when force is applied to the lever 98 is then actuated to bring the upper blade down to the lower cutter blade 88 cutting the nail. Resultantly, a cut out 96 in the finished cut will appear as shown in FIG. 7-D. In this regard, it has been discovered that where such said cut out 96 is made in the nail, future nail growth is directed outwardly towards the sides of the nail into the soft tissue which borders the sides of the nail. Thus, where there is a pre-existing ingrown nail, the redirection of the growth precipitated by a cut out relieves the pressure of the nail on the damage on the soft tissue thereby relieving the pain and accelerating the healing process. Further, even where there is no pre-existing ingrowth of the nail, the redirecting of future growth towards the sides of the nail can prevent future ingrowth of the nail into the bordering soft tissue.

The preferred method for treating the hang nail is to open the nail clipper/cutter device 70, and by lifting lever arm 98 from the rearwardly position flip arm 98 one hundred eighty degrees forwardly towards the cutter blades tips 78 and 88 and rotating the lever 98 one hundred eighty degrees, the lever will rest on the protruding member 108. The cutter device will be held in an open blade position by means of a protruding member 108 as shown in FIG. 7-A. Place the open cutter blades adjacent to hang nail to be treated with. The cutter blades disposed proximately ninety degrees perpendicular to the hang nail to be treated. The side of the nail, cutter tip is held against the base of the hang nail and when force is applied to the lever 98 it is then actuated to bring the upper blade down to the lower cutter blade 88 cutting the hang nail off. Release the force to open the cutter blades and dispose the hang nail cut out 96.

Second Embodiment Conclusions, Ramifications, and Scope

Accordingly, it can be seen that the nail clipper/cutter device, is easy to use, without the use of chemicals, and reduces the invasive nature of treating and/or preventing ingrown nails. Furthermore, the nail cutter/clipper device has additional advantages in that:

- it provides simpler, more reliable, easy use;
- it provides use for people with certain disabilities;
- it provides two V-shaped cutter blades for true cutter action on different nail textures;
- it provides two sharp V-shaped cutter blades for medical precision;
- it may also be used for cutting off hang nails and/or other felons;
- it provides stainless steel cutter blades for easy medical sterilization;
- it provides long lasting stainless steel;
- it allows left or right handed use;
- it saves time over other methods;
- it provides self containment of nail cuttings for later disposal;
- it permits use on primates and other animals;
- it provides method of treating and/or preventing ingrown nails;
- it provides rust resistant stainless steel;
- it provides fast results;
- it permits use on two(right & left sides) simultaneously ingrown nails on a single nail;

Although the description above contains many specificity's, these should not be construed as limiting the scope of the invention but as merely providing illustrations of some of the presently preferred embodiments of this invention. Various other embodiments and ramifications are possible within it's scope. For example, a resilient metal, or glass reinforced nylon could be used in place of surgical steel. Also the handle covering could be made from a rubber material, selected elastomer material, or no covering. Also the symmetrical sixty degree V-shaped cutter blade angle could be seventy degrees. Nail clipper size can be small, medium or large, and it can include a means to actuate the actuator for people with disabilities, a mechanical means to increase ratio of force, for use on primates, and other animals with human like nails. The scope of the foregoing description of the preferred embodiment of the invention has been presented for the purposes of illustration and description. It will be understood that there is no intention to limit the invention to such disclosure but rather it is intended to cover all alternate construction and modifications falling within the scope and the spirit of the invention as defined in the appended claims.

Second Embodiment Summary

A nail clipper/cutter device comprising a first member having a forward end portion defining a upper jaw, V-shaped blade portion and a second member having a forward end portion defining a lower jaw, V-shaped blade portion and actuating means for moving upper jaws and lower jaws, V-shaped blade portions through the nail whereby said nail cutter/clipper device makes a cutout in a nail and the associated method for treating ingrown nails and hang nails and/or preventing ingrown nails.

Preferred Third Embodiment Folding Nail clipper—Description

Figure 8:
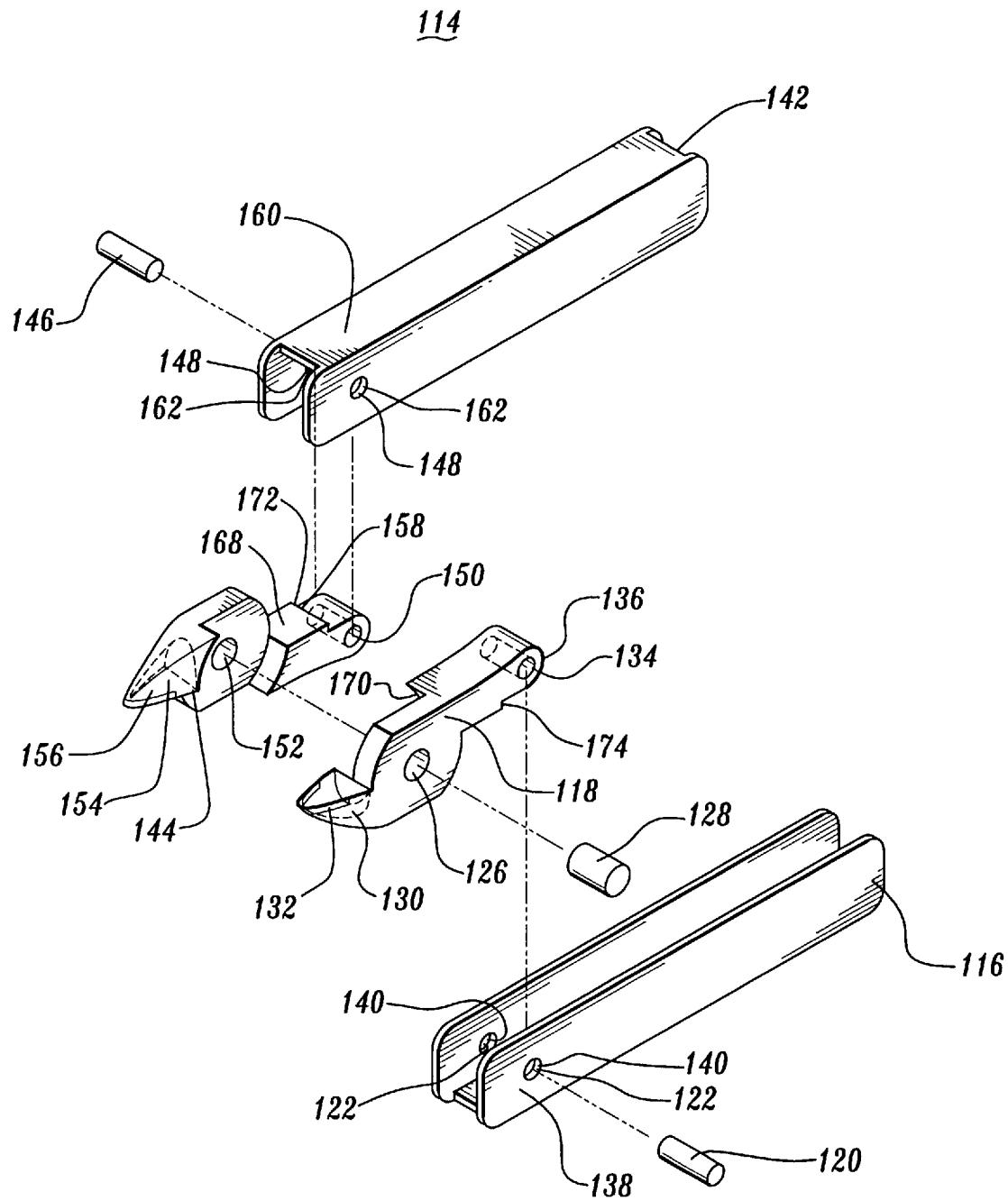
FIG. 8 is an isometric view of the folding nail clipper/cutter device of the present invention.
Figure 8A:
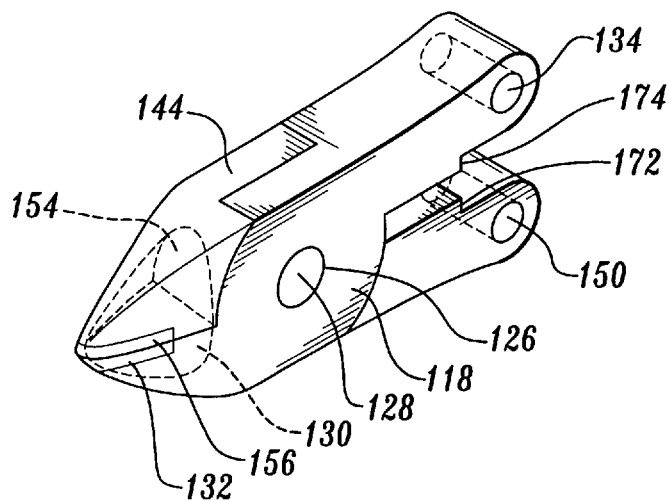
FIG. 8A is an enlarged detail of the head portion of the folding nail clipper/cutter device of the present invention.
Figure 8B:
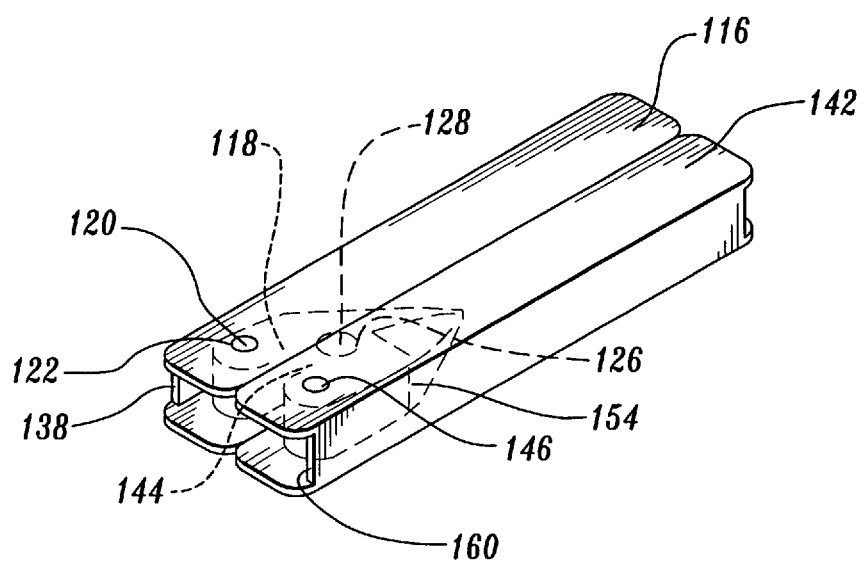
FIG. 8B is an isometric view of the folded nail clipper/cutter device of the present invention.
Figure 8C:
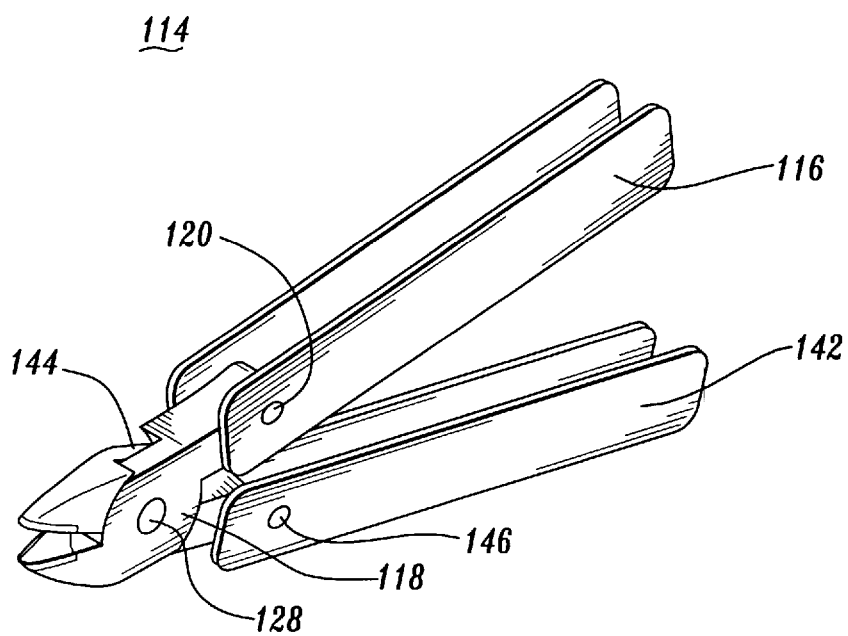
FIG. 8C is an isometric view of the open folding nail clipper/cutter device of the present invention.

The general description of FIG. 8, shows an exploded view of cutter/clipper device 114. The folding nail clipper/cutter device 114 comprises, a U-shaped handle member 116, cutter head portion 118, a gudgeon 120 for joining said handle 116 and said cutter head portion 118 together. A U-shaped handle member 142, cutter head portion 144, a gudgeon means 146 for joining said handles 116 and cutter head portion 142 together. Mated together by a pivotal means 128 for joining said equal length handles member 142 and member 142, and equal length head portion 118 and 144 in an x shaped placement.

FIG. 8 also shows a nail cutter/clipper device 114 with a portion consisting, a head portion, cutter head portion 118, a V-shaped void, V-void or void 130, a cutter head blade, V-blade or blade 132, a hole, cutter hole or gudgeon hole 126, a protruding head member 170 consisting of a tongue 174, an arc 136, a hole 134, and joined to a handle portion consisting of a U-shaped handle 116, a hole 122, a spacer 140, a gudgeon 120, mates to the said cutter head portion 118, a mating tongue 174 mates into a notch 138 a means of setting the angle of the handle 116. Another portion consisting of a cutter head portion 144, a void 154, a cutter head blade 156, a hole 152, a protruding head member 168 consisting of a tongue 172, an arc 158, a hole 150, and joined to a handle portion consisting of a U-shaped handle 142, a hole 148, a spacer 162, a gudgeon 146, mates to the said cutter head portion 144, a mating tongue 172 into a notch 160 a means of setting the angle of the handle 142. All of the above fabricated from die-casted surgical steel. The said first and second portions are mated by said gudgeon 128 and inserted into said hole 126 and 152, all of the above is made from die casted surgical steel.

The approximate overall dimensions of the nail cutter device in one commercial embodiment were as follows: from handle to the cutter tip overall length 100 mm, the widest point of the handles from outer edge to the outer edge is 44 mm, 42 mm radius at high point of handle arc, cutter blade 9 mm long, cutter head 25 mm long and thickness 5 mm, gudgeon 5 mm diameter outside dimension, the mating plate's 2.5 mm each, material not known, manufactured in Germany.

FIG. 8-A shows partial enlarged detail of the said nail cutter head portion in a closed position. In accordance with the invention the said nail cutter head portion, cutter head portion 118, a V-shaped void, V-void or void 126, a cutter head blade, V-blade or blade 132, a hole, cutter hole or gudgeon hole 126, a protruding head member 170 consisting of a tongue 174, an arc 136, a hole 134, the other mating portion consisting of a cutter head portion 144, a void 154, a cutter head blade 156, a protruding head member 168 consisting of a tongue 172, an arc 158, a hole 150 which are joined by the gudgeon 128.

FIG. 8-B shows detail of the said folding nail cutter head portion in a folded position. In accordance with the invention the said nail cutter head portion, cutter head portion 118, a V-shaped void, V-void or void 130, a cutter head blade, V-blade or blade 132, a hole, cutter hole or gudgeon hole 130, a protruding head member 170 consisting of a tongue 174, an arc 136, the other mating cutter head portion 144 consisting of a void 154, a cutter head blade 156, a hole 152, a protruding head member 168 consisting of a tongue 172, an arc 158, which are joined by the gudgeon 128. The head portions mate into the open handle portions thereby enclosing the said heads into the said handles.

FIG. 8-C shows isometric of the said folding nail clipper/cutter head portion in an open position. In accordance with the invention the said nail cutter head portion 118, a void, a cutter blade, a hole, a protruding head member consisting of a tongue, an arc, a hole, the other mating cutter head portion 144, a void, a cutter blade, a hole, a protruding head member consisting of a tongue, an arc, a hole and which are joined by the gudgeon 128. The head portions mate into the open handle portions 116 and 142, thereby enclosing the said heads into the said handles.

Preferred Third Embodiment Folding Nail clipper—Operation

Operation and use of the nail cutter/clipper device and associated method for treating ingrown nails and hang nails and/or preventing ingrown nails is simple and straight forward. FIG. 8-B shows in a closed position, open the nail cutter device by spreading handles apart with one hand on each handle, pull apart with just enough force to separate the handles an rotate the handles one hundred eighty degrees opposite direction of cutter tips in FIG. 8-C. The handles will rotate around the gudgeons 120 and 146,and the handles will mate the notch into the tongue as a means for setting, and holding the angle of the handles in place. Releasing the lower handle thereby opening the cutter blades by rotating around the gudgeon 128 then place the open cutter blades with nail to be treated proximate to the side of the ingrown nail and place open blades in between the nail, the tip of the cutter blade is inserted to a proximate comfortable depth in the nail and when force is applied by hand or machine to the handles in a closing motion the device will close together rotating about the gudgeon 128, and by increasing the forces on the handles and this increases the forces on the cutter head portion, increase the force cutting through the nail thereby capturing the nail cutting and the nail cutter blades will appear as shown in FIG. 8-A, then decrease the force to open the blades as shown in FIG. 8-C, dispose the nail cutting.

The preferred method for treating the hang nail is to open the nail cutter and place the cutter blades proximately ninety degrees perpendicular to the hang nail to be treated and hold the side of the nail clipper blade held against the base of the hang nail, then close the nail cutter by applying pressure on handles, the nail cutter blades will appear as shown in FIG. 8-A, increase the force to cut the hang nail off, decrease the force to open the blades as shown in FIG. 8-C, dispose the hang nail cutting.

Third Embodiment Conclusions, Ramifications, and Scope

Accordingly, it can be seen that the nail clipper/cutter device, is easy to use, without the use of chemicals, and reduces the invasive nature of treating and/or preventing ingrown nails. Furthermore, the nail cutter/clipper device has additional advantages in that:

it provides simpler, more reliable, easy use;

it provides use for people with certain disabilities;

it provides two V-shaped cutter blades for true cutter action on different nail textures;

it provides two sharp V-shaped cutter blades for medical precision;

it may also be used for cutting off hang nails and/or other felons;

it provides stainless steel cutter blades for easy medical sterilization it provides long lasting stainless steel;

it allows left or right handed use;

it saves time over other methods;

it provides self containment of nail cuttings for later disposal;

it permits use on primates and other animals;

it provides method of treating and/or preventing ingrown nails;

it provides rust resistant stainless steel;

it provides fast results;

it permits use on two (right & left sides) simultaneously ingrown nails on a single nail;

Although the description above contains many specificity's, these should not be construed as limiting the scope of the invention but as merely providing illustrations of some of the presently preferred embodiments of this invention. Various other embodiments and ramifications are possible within it's scope. For example, a resilient metal, or glass reinforced nylon could be used in place of surgical steel. Also the handle covering could be made from a rubber material, selected elastomer material, or no covering in place of latex. Also the symmetrical sixty degree V-shaped cutter blade angle could be sixty five degrees, Nail clipper size can vary small medium or large, a means to actuate the actuator for people with disabilities, a mechanical means to increase ratio of force, for use on primates, and other animals with human like nails.

The scope of foregoing description of the preferred embodiment of the invention has been presented for the purposes of illustration and description, it will be understood that there is no intention to limit the invention to such disclosure but rather it is intended to cover all alternate construction and modifications falling within the scope and the spirit of the invention as defined in the appended claims.

Third Embodiment Summary

A nail clipper/cutter device -fold up version comprising a support member with V-shaped cutter blade and folding handle and a support member with V-shaped cutter blade and folding handle and a pivotal means for joining said two equal length support members in an x shaped placement with folding handles whereby said nail cutter/clipper device makes a cutout in a nail and the associated method for treating ingrown nails and hang nails and/or preventing ingrown nails.

What is claimed is:

1. Apparatus for cutting notches in a nail on a foot or a hand, comprising:
   (a) a first cutting head having a first jaw with edges that define a first cavity which is generally V-shaped and adapted to receive cuttings;
   (b) a second cutting head having a second jaw with edges that define a second cavity that is generally V-shaped and also adapted to receive the cuttings, said first cutting head being movably coupled to said second cutting head by a pivot pin, with the first jaw disposed generally opposite the second jaw, and the first cutting head crossing the second cutting head proximate to the pivot pin;
   (c) a first handle coupled to the first cutting head;
   (d) a second handle coupled to the second cutting head, said first and second handles being adapted to be gripped and squeezed by the user to apply the force for cutting the nail; and
   (e) handle pivot pins that pivotally connect the first and second handles respectively to the first and the second cutting heads, said first and second handles each including a void in which the first and the second cutting heads are received when the first and the second handles are pivoted over the first and the second cutting heads, for storage and transport while the apparatus is not being used for cutting the nail.

2. The apparatus of claim 1, wherein said first and second handles are each at least partially covered by an elastomeric material that provides a soft gripping surface.

3. Apparatus for cutting notches in a nail on a foot or a hand, comprising:
   (a) a first cutting head having a first jaw with edges that define a first cavity which is generally V-shaped and adapted to receive cuttings;
   (b) a second cutting head having a second jaw with edges that define a second cavity that is generally V-shaped and also adapted to receive the cuttings, said first cutting head being movably coupled to said second cutting head by a pivot pin, with the first jaw disposed generally opposite the second jaw, and the first cutting head crossing the second cutting head proximate to the pivot pin;
   (c) a first handle coupled to the first cutting head; and
   (d) a second handle coupled to the second cutting head, said first and second handles each being at least partially covered by an elastomeric material that provides a soft gripping surface and adapted to be gripped and squeezed by the user to apply the force for cutting the nail.

4. Apparatus for cutting nails on a hand or a foot, comprising:
   (a) a pair of opposed members adapted to be held in a hand of a user, each of the opposed members comprising a jaw formed at one end thereof disposed opposite the jaw on the other of the opposed members;
   (b) each jaw including a receptacle that is extended and enlarged, the receptacles being disposed in facing surfaces of the jaws and adapted to receive nail cuttings; and
   (c) a blade defined by two generally straight lines that form an angle of about 60 degrees and extend from a tip of the jaw along opposite edges of the receptacle disposed in each jaw, said blade defining a cutting line centered about the receptacle and adapted for cutting a V-shaped notch in the nails to produce the nail cuttings when the blade on one jaw is forceably urged toward the blade on the other jaw, said of opposed members being movably coupled together so as to enable the user to forceably urge the blade on one jaw toward the blade on the other jaw with a force sufficient to cut the nails.

5. The apparatus of claim 4, wherein the cutting line defined by the blade on each jaw has a generally V-shape configuration.

6. The apparatus of claim 4, wherein the opposed members are biased by a spring force applied in a direction that tends to urge the jaws apart from each other.

7. The apparatus of claim 6, wherein the spring force is applied by a spring that is disposed between the opposed members.

8. The apparatus of claim 6, further comprising a lever coupled to the opposed members at a pivot, said lever providing a surface and a mechanical advantage that enables the user to urge said jaws toward each other with the force sufficient to cut the nails.

9. The apparatus of claim 8, wherein the spring force arises from a characteristic elasticity of the opposed members, the opposed members being connected together with a fastener that is disposed adjacent one end opposite that at which said jaws are disposed, the opposed members being shaped so that the jaws are urged apart by said characteristic elasticity of the opposed members in opposition to said force applied by the user pressing on the lever.

10. The apparatus of claim 9, wherein said opposed members generally comprise surgical metal strips having the jaws and the blades formed thereon, said blades defining the receptacles in said jaws.

11. The apparatus of claim 8, wherein the pivot comprises a pin that couples the lever to the opposed members and limits a separation between the opposed members and the jaws.

12. The apparatus of claim 4, further comprising a pivot pin that pivotally connects said opposed members together, said pivot pin being disposed adjacent to said jaws.

13. The apparatus of claim 12, wherein the opposed members each comprise a handle that is pivotally coupled to one end of a cutter head at a handle pivot pin, one of the jaws extending from an opposite end of the cutter head.

14. The apparatus of claim 13, wherein each handle includes a void disposed adjacent to the handle pivot pin and sized to receive the cutter head and said one of the jaws, said handle being pivoted around the handle pivot pin to encompass the cutter head and said one of the jaws in said void when the apparatus is not being used.

15. The apparatus of claim 4, wherein the opposed members are coated with an elastomeric material that provides a gripping surface for the hand of the user.

16. The apparatus of claim 4, further comprising a latch for retaining said opposed members in a storage position in which a separation between the facing surfaces of the jaws is substantially limited.

17. Apparatus for cutting notches in a nail on a foot or a hand, comprising:
   (a) a first cutting head having a first jaw with edges that are generally straight and which form an angle of about 60 degrees, said edges defining a first cavity that is generally V-shaped, elongate, and extended, and which is adapted to receive cuttings;
   (b) a second cutting head having a second jaw with edges that are generally straight and which form an angle of about 60 degrees, said edges defining a second cavity that is generally V-shaped, elongate, and extended, and which is also adapted to receive the cuttings, said first cutting head being movably coupled to said second cutting head with the first jaw disposed generally opposite the second jaw; and (c) means for enabling a user to urge the first jaw and the second jaw toward each other, the edges of said first and said second jaws applying a force against a nail disposed therebetween sufficient to cut through the nail, producing a cutting that is deposited in one of the first and the second generally V-shaped cavities.

18. The apparatus of claim 17, further comprising a pivot pin for pivotally coupling the first cutting head to the second cutting head.

19. The apparatus of claim 18, wherein the first cutting head crosses the second cutting head proximate to a point where the pivot pin pivotally couples the first cutting head to the second cutting head, said first cutting head and said second cutting head each being connected to a different one of two handles, said means for enabling comprising the handles, which are adapted to be gripped and squeezed by a user to apply the force for cutting the nail.

20. The apparatus of claim 19, wherein the handles are at least partially covered with an elastomeric material that provides a soft gripping surface on the handles.

21. The apparatus of claim 19, wherein said means for enabling further include handle pivot pins that pivotally connect the handles to the first and the second cutting heads, said handles including a void in which the first and the second cutting heads are received when the handles are pivoted over the first and the second cutting heads, for storage and transport while the apparatus is not being used for cutting the nail.

22. The apparatus of claim 17, wherein the means for enabling include:

(a) two members flexibly coupled together, said first cutting head being joined to one of the members and said second cutting head being joined to the other of the members; and (b) a lever for applying a force against the members that forces the members and the first and the second cutting heads toward each other to cut the nail.

23. The apparatus of claim 22, wherein the means for enabling further include a linking pin that extends through orifices formed in the two members and couples the lever to a surface of one of the two members, said linking pin providing a pivot point for the lever and limiting a separation between the two members.

24. The apparatus of claim 17, further comprising a spring for urging the first jaw apart from the second jaw.

* * * * *